United States Patent
Peters et al.

[11] Patent Number: 6,080,184
[45] Date of Patent: Jun. 27, 2000

[54] PACKAGE FOR RETAINING A SUTURE AND A SUTURE ANCHOR

[75] Inventors: Robert C. Peters; Robert C. Hackett; David G. Phillips, all of Tampa, Fla.

[73] Assignee: Linvatec Corporation, Largo, Fla.

[21] Appl. No.: 09/104,633

[22] Filed: Jun. 25, 1998

[51] Int. Cl.[7] .................................................. A61B 17/04
[52] U.S. Cl. ........................................ 606/228; 206/63.3
[58] Field of Search ............................... 606/232, 73, 75, 606/148, 228, 230; 206/63.3, 227, 380, 388, 382

[56] References Cited

U.S. PATENT DOCUMENTS

| | | |
|---|---|---|
| 3,206,018 | 9/1965 | Lewis et al. ............................ 206/63.3 |
| 3,363,751 | 1/1968 | Shave et al. . |
| 4,120,395 | 10/1978 | Mandel et al. . |
| 5,092,455 | 3/1992 | Leary . |
| 5,121,836 | 6/1992 | Brown et al. . |
| 5,341,622 | 8/1994 | Odermatt et al. . |
| 5,390,782 | 2/1995 | Sinn . |
| 5,566,821 | 10/1996 | Brown et al. . |
| 5,697,950 | 12/1997 | Fucci et al. . |
| 5,707,394 | 1/1998 | Miller et al. . |

*Primary Examiner*—Michael Buiz
*Assistant Examiner*—Vikki Trinh
*Attorney, Agent, or Firm*—Larson & Larson, P.A.; James E. Larson

[57] ABSTRACT

A package consists of a plastic "card" made up of a flat, rectangular piece of material having a centrally located scoring allowing the piece of material to be folded upon itself to provide an inner enclosure. The card includes two halves to either side of the scoring, a first half including cut-outs forming two tabs that enmesh with two slots formed in the second half so that when the card is folded about the scoring, the tabs may be inserted into the slots to hold the card in the folded configuration. The second half has a series of slots of various configurations and located in desired locations to allow retention of a guide wire, suture and suture anchor in a desired configuration. Adjacent slots provided for receipt of the guide wire are laterally misaligned to cause the guide wire to be slightly bowed when inserted through these adjacent slots, thereby facilitating a creation of frictional forces that act to retain the guide wire in its mounted position on the second half of the card, absent application of a removing force. Slots are provided permitting the suture to be easily removed from the card by pulling it in one direction. At the end of the suture, the suture anchor is retained by a loop of the suture extending through an opening in the proximal end of the suture anchor. Slots are formed on a top edge of the second half of the card and the suture is wound across this third pair of slots between the guide wire and the second pair of slots. Between the two slots forming a third pair of slots, the user may easily grasp the suture and, with a pulling motion, may remove the guide wire, the suture and the suture anchor.

15 Claims, 4 Drawing Sheets

PACKAGE FOR RETAINING A SUTURE AND A SUTURE ANCHOR

BACKGROUND OF THE INVENTION

The present invention relates to an insert/dispenser card for loaded anchors. U.S. Pat. Nos. 5,697,950 to Fucci et al. and 5,707,394 to Miller et al. disclose pre-loaded suture anchors with rigid extensions. As should be understood from review of these patents, the disclosures of which are incorporated by reference herein, it is known to interconnect a suture anchor with a guide wire using a length of suture so that the suture anchor can be easily mounted on an anchor driver. In use, the guide wire is inserted through a passageway through the driver and the suture is pulled therethrough, as well, until the suture anchor reaches the anchor driver and is coupled thereto. Thereafter, the guide wire is removed along with any section of the suture that has been handled during this operation.

During orthopedic surgery, the surgeon must "load" a suture anchor on an anchor driver in the manner described above while wearing surgical gloves, thus making the process potentially cumbersome. While the combination of the guide wire, suture and suture anchor has been devised specifically to make easier the process of coupling a suture anchor to the anchor driver, a need has developed for a sterilizable package for the combination of the guide wire, suture and suture anchor that allows the surgeon, or a nurse or attendant wearing similar garb, to easily remove the guide wire, suture and suture anchor from the sterilized package so that it may be suitably manipulated in the manner described above to result in coupling of the suture anchor to the anchor driver. It is with this need in mind that the present invention was developed.

The following prior art is known to Applicants:

U.S. Pat. No. 5,341,622 to Odermatt et al. discloses a package designed to hold a plurality of sutures. U.S. Pat. Nos. 3,363,751 to Shave et al.; 4,120,395 to Mandel et al.; 5,092,455 to Leary, 5,121,836 to Brown et al.; 5,390,782 to Simn; and 5,566,821 to Brown et al. each disclose a package containing at least one needle with a suture pre-loaded thereon. These patents disclose various ways of retaining a suture therein including winding the suture, looping it back and forth, etc. The present invention differs from the teachings of these patents as contemplating a package for a combined guide wire, suture and suture anchor wherein the guide wire is contained within the package in a slightly bowed configuration to best facilitate frictional retention of the guide wire within the package. The present invention further contemplates placement of the suture within the package in such a manner that one portion of the suture may be suitably grasped whereupon the entire guide wire-suture-suture anchor assembly may be removed easily from the package, ready for use.

SUMMARY OF THE INVENTION

The present invention relates to an insert/dispenser card for loaded anchors. The present invention includes the following interrelated objects, aspects and features:

(1) In a first aspect, the inventive package consists of a "card" made up of a flat, generally rectangular piece of material having a centrally located scoring allowing the piece of material to be folded upon itself to provide an inner enclosure. In the preferred embodiment, the material comprises a thin, sterilizable plastic material.

(2) The inventive card includes two halves to either side of the scoring, a first half and a second half The first half includes cut-outs forming two tabs that enmesh with two slots formed in the second half so that when the card is folded about the scoring, the tabs may be inserted into the slots to hold the card in the folded configuration.

(3) The second half has a series of slots of various configurations and particularly located in desired locations through the second half to allow retention of the guide wire, suture and suture anchor in a desired configuration. Thus, cut-outs are formed along the length of the second half and are designed to receive the guide wire by inserting the guide wire back and forth from a front face of the second half to a back face of the second half and then back again to the front face to facilitate retention of the guide wire on the card. In one important aspect of the present invention, adjacent slots provided for receipt of the guide wire are laterally misaligned to cause the guide wire to be slightly bowed when inserted through these adjacent slots, thereby facilitating a creation of frictional forces that act to retain the guide wire in its mounted position on the second half of the card, absent a removing force being applied thereon.

(4) A second series of slots of S-shaped configuration are provided in alignment with one another which permit the suture to be inserted through these aligned slots in a first direction and then doubled back in a second direction, thereby allowing the suture to be easily removed from the card by pulling it in one direction. At the end of the suture, at a location above the top-most one of the slots forming the second set of slots, the suture anchor is retained by a loop of the suture extending through an opening in the proximal end of the suture anchor.

(5) A third set of slots are formed on a top edge of the second half of the card and the suture is wound across this third pair of slots between the guide wire and the second pair of slots. Between the two slots forming a third pair of slots, the user may easily grasp the suture and, with a pulling motion, in the plane of the second half of the card, may remove the guide wire, the suture and the suture anchor.

(6) In use, the guide wire-suture-suture anchor combination is loaded on the second half of the card in the manner described above and the first half is folded over the second half at the scoring with the tabs of the first half received into the slots of the second half to close the first half over the second half thereby enclosing the guide wire-suture-suture anchor combination. When it is desired to use this combination, the user may grasp the suture at the location between the slots of the third pair of slots and may pull upwardly away from the card in a direction generally coplanar with the second half of the card to easily remove the guide wire-suture-suture anchor combination therefrom with little resistance. The first half may have a slot or cut-out aligned with the third pair of slots when the first half is fastened over the second half allowing the suture to be grasped between the slots comprising the third set of slots when the first half is covering the second half of the card.

Accordingly, it is a first object of the present invention to provide an insert/dispenser card for loaded anchors.

It is a further object of the present invention to provide such a card wherein a guide wire-suture-suture anchor combination may be loaded thereon so that it can be easily removed with little resistance to such removal.

It is a yet further object of the present invention to provide such a device wherein the card is divided into one half that receives the guide wire-suture-suture anchor and another half that may be pivoted thereover to enclose the guide wire-suture-suture anchor.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
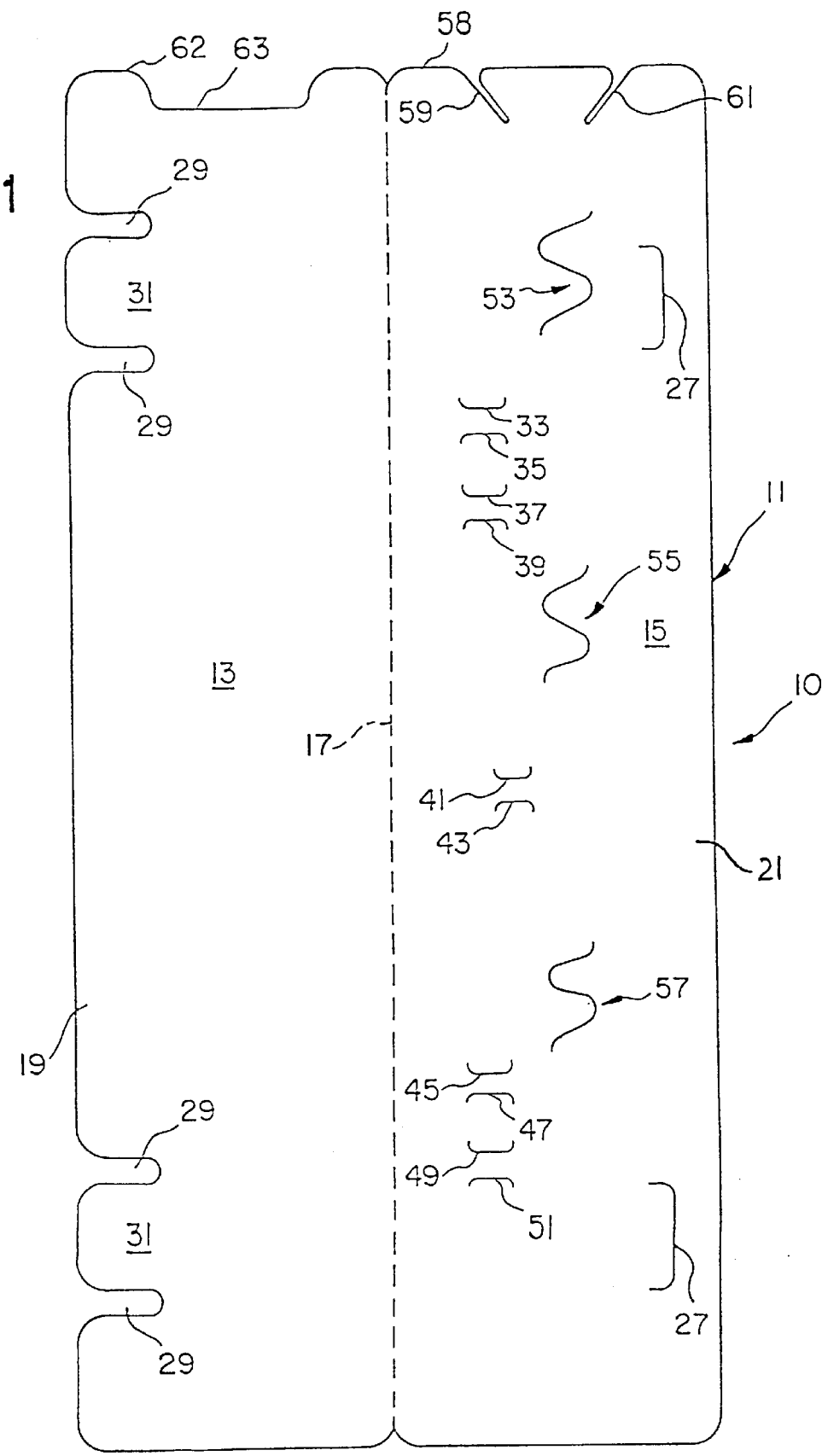
FIG. 1 shows a top view of an insert/dispenser card in accordance with the teachings of the present invention.
Figure 5:
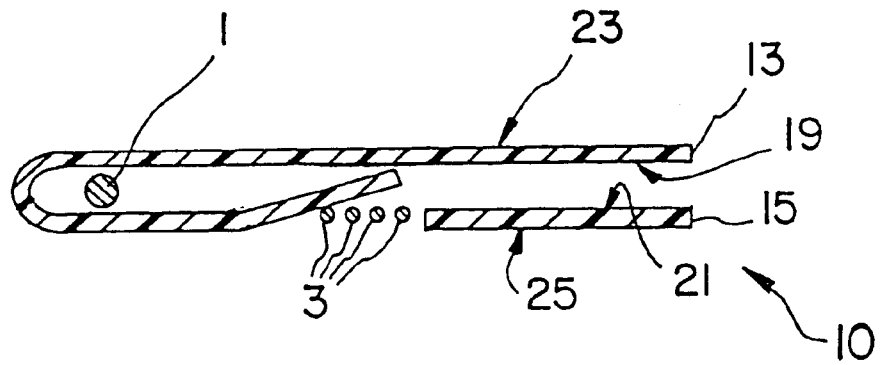
FIG. 5 shows a cross-sectional view along the line V—V of FIG. 3.

With reference, first, to FIG. 1, the present invention is generally designated by the reference numeral 10 and comprises a body 11 consisting of a thin card having a first half 13 and a second half 15 separated by a scoring 17 that allows the first half 13 to be folded over the second half 15. For ease of understanding, the first half 13 has a top face 19 shown in FIG. 1 and the second half 15 has a top face 21 shown in FIG. 1. Each of the halves 13 and 15 has a bottom face (FIG. 5) with the first half 13 having a bottom face 23 and with the second half 15 having a bottom face 25. FIG. 5 shows the first half 13 folded over the second half 15 so that the bottom face 23 of the first half 13 actually overlies the bottom face 25 of the second half 15 in the view shown in FIG. 5. However, as may be easily imagined, when the halves 13 and 15 are in the position shown in FIGS. 1 and 2, the bottom faces 23 and 25 are side-by-side.

Figure 3:
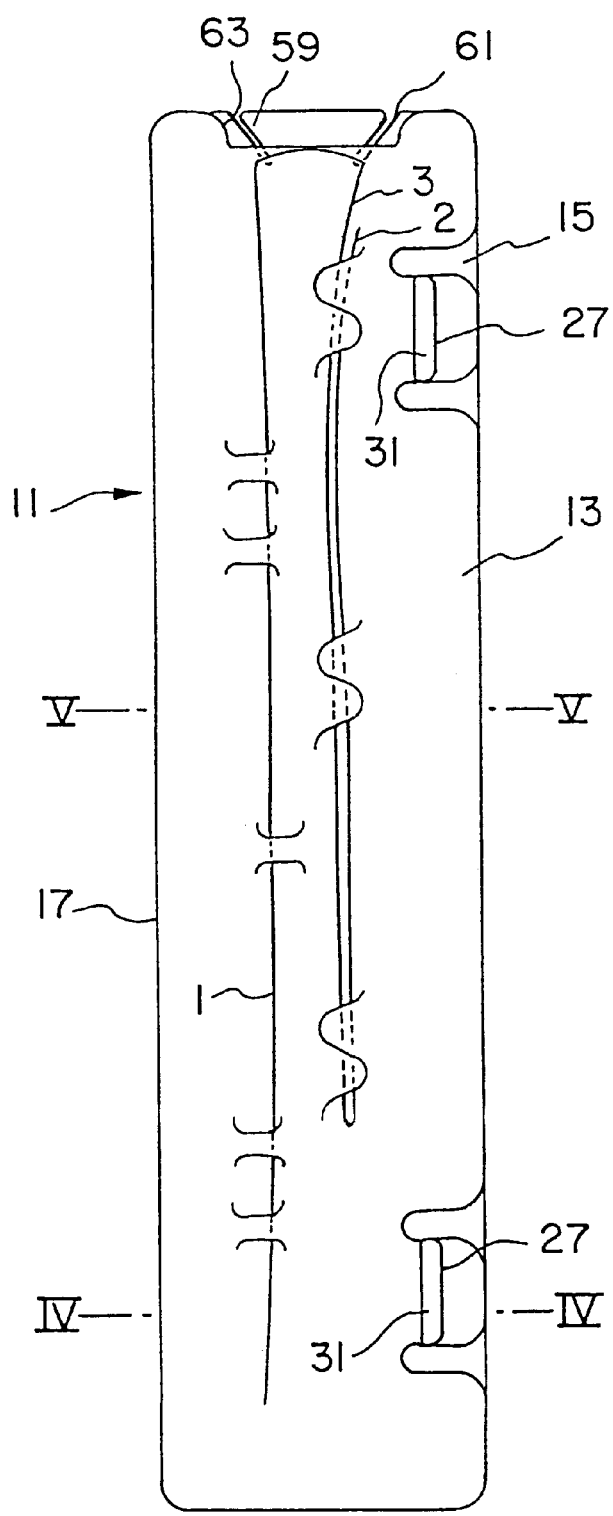
FIG. 3 shows an insert/dispenser card with the first half folded over the second half and secured together.
Figure 4:
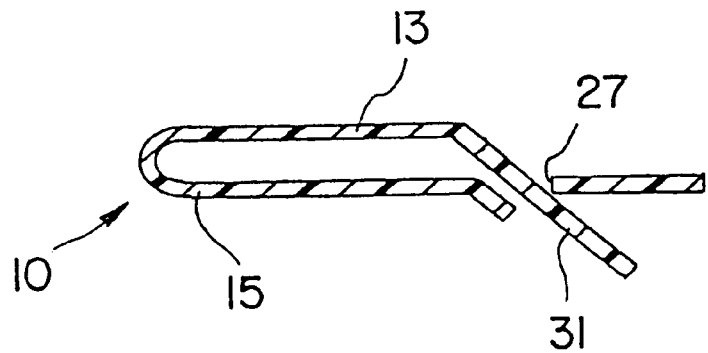
FIG. 4 shows a cross-sectional view along the line IV—IV of FIG. 3.

With reference, back, to FIG. 1, the second half 15 includes closure slots 27 formed therethrough and the first half 13 has cut-outs 29 that form tabs 31 vertically aligned with the closure slots 27 in the view of FIG. 1, so that when the first half 13 is folded over the second half 15 at the scoring 17, the tabs 31 may be inserted into respective ones of the closure slots 27 to secure the card 10 in the folded over position shown in FIG. 3. FIG. 4 shows a tab 31 inserted through a closures slot 27.

With reference back to FIG. 1, the second half 15 of the card 11 has a first set of slots comprising a plurality of pairs of slots formed therein for a purpose to be described in greater detail 5 hereinafter. In FIG. 1, these pairs of slots creating tabs therebetween are designated by the reference numerals 33,35; 37,39; 41,43; 45,47; and 49, 51. As seen in FIG. 1, the slots 33,35, 37 and 39 are laterally aligned with one another as are the slots 45,47,49 and 51. Similarly, the slots 41 and 43 are laterally aligned with one another, however, the slots 41 and 43 are laterally misaligned with the slots 39 and 45 as well as with the slots aligned with the slots 39 and 45, respectively. This misalignment of the slots 41 and 43 is for a purpose to be described in greater detail hereinafter.

Additionally, a second set of slots are formed in the second half 15 of the card 11 and are designated by the reference numerals 53, 55 and 57. These slots are all generally "S" shaped and are laterally aligned with one another for a purpose to be described in greater detail hereinafter. Each of the slots 53, 55 and 57 is laterally misaligned with respect to the first set of slots.

The second half of the card also includes a third set of slots consisting of the slots 59 and 61. These slots are formed on a top edge 58 of the second half 15 of the card 11. The first half of the card includes a slot or cut-out 63 formed in the top edge 62 of the first half 13 of the card 11.

Figure 2:
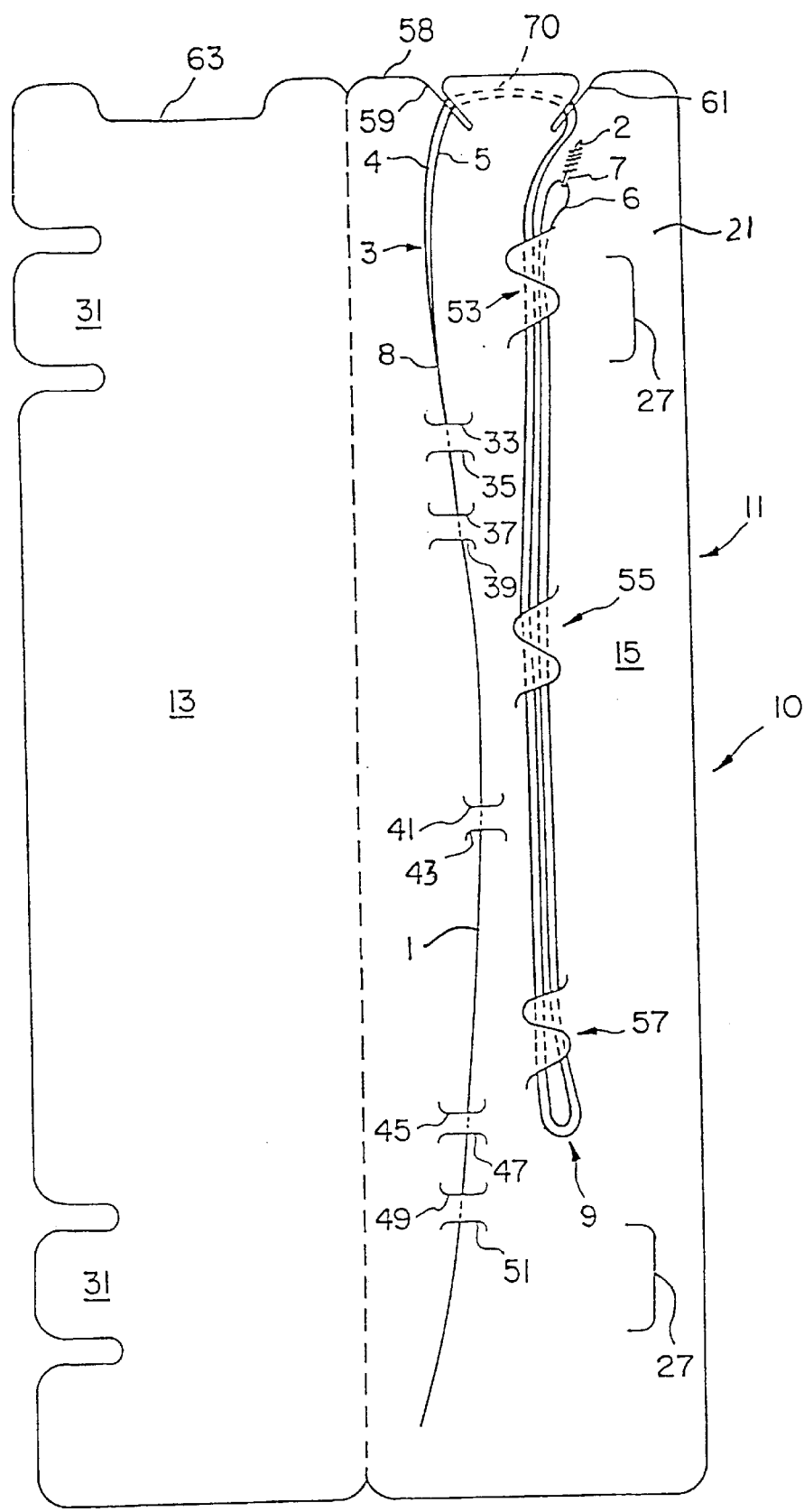
FIG. 2 shows a view similar to that of FIG. 1 but with a guide wire-suture-suture anchor suitably loaded thereon.

With reference, now, to FIG. 2, a guide wire 1 is seen to be coupled to a suture anchor 2 by a suture 3 including a first leg 4 and a second leg 5 meeting at a loop 6 that extends through an opening 7 in a proximal end of the suture anchor 2 to capture the suture anchor 2. The suture 3 is coupled to the guide wire 1 at a coupling 8 that is made in any suitable manner such as, for example, is shown in U.S. Pat. No. 5,707,394.

As seen in FIG. 2, the guide wire 1 is inserted through the slots 33, 35, 37, 39, 41, 43, 45, 47, 49 and 51. Because of the lateral misalignment of the slots 41, 43 with respect to the other slots, the normally straight guide wire 1 adopts the arcuate configuration shown in FIG. 2. The arcuate configuration of the guide wire 1 facilitates frictional retention of the guide wire 1 on the card 11 to prevent inadvertent or accidental removal while not bending the wire to a degree imparting a permanent bend.

As also seen, with particular reference to FIG. 2, the suture 3 extends from its coupling 8 with the guide wire 1 and is first looped around the slots 59, 61 such that a portion of the suture is behind the second half 15 of the card 11 on the bottom face 25 thereof. When the legs 4, 5 of the suture 3 emerge from the slot 61 back to the top face 21 of the second half 15 of the card 11, these suture legs 4, 5 travel through the slot 53, the slot 55 and the slot 57 whereupon they loop around at the location of the reference numeral 9, then proceeding back upwardly along the second half 15 of the card 11, back through the slots 57, 55 and 53 to the location of the loop 6 of the suture legs 4, 5 where the suture anchor 2 is captured. As should be understood, from FIG. 2, this configuration precludes the suture anchor 2 from having to be pulled through any of the slots on the card. Thus, in the configuration shown in FIG. 2, when the suture 3 is grasped at the location 70 at the top of FIG. 2, and the suture 3 is pulled in the upward direction in the view of FIG. 2, in the plane of the second half 15 of the card 11, the guide wire 1 is sequentially removed from the slots 51, 49, 47, 45, 43, 41, 39, 37, 35, 33, while at the same time, the suture 3 is pulled sequentially from the slots 57, 55, 53, with the loop 9 traveling upwardly in the view of FIG. 2 until the loop 9 arrives at the location of the suture anchor 2 in the view of FIG. 2 whereupon the entire combination of the guide wire 1, suture 3 and suture anchor 2 is easily lifted from the card 11. The guide wire 1 may then easily be inserted through a passageway in the suture driver (not shown) with the suture 3 being pulled theretlrough as well until the suture anchor 2 arrives at the location where it is coupled to the suture anchor driver and can then be driven into a bone during the performance of orthopedic surgery.

As should be self-evident, from the above description, FIG. 3 shows the first half 13 of the card 11 folded over the second half 15 at the scoring 17 with the tabs 31 inserted in the slots 27 to hold the card 11 in the position shown. In FIG. 3, the guide wire 1, suture 3 and suture anchor 2 are shown in phantom as are the various slots located on the second half 15 of the card 11. As shown in FIG. 3, the slot 63 facilitates grasping of the suture 3 between the slots 59, 61 with the card half 13 overlying the card half 15.

In the preferred embodiment of the present invention, the card is made of any suitable thin, flexible and sterilizable plastic material. The various slots, tabs and cut-outs in the card may be formed in any suitable manner such as, for example, in a die cutting apparatus. The same apparatus may easily form the scoring 17 during the manufacturing process.

As such, an invention has been disclosed in terms of a preferred embodiment thereof which fulfills each and every one of the objects of the invention as set forth hereinabove and provides a new and useful insert/dispenser card for loaded anchors of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

We claim:

1. A suture retaining package comprising:
    a) a thin body having a front face, a rear face, and a top edge;
    b) a first set of paired slots forming a tab between each pair for holding a guide wire;
    c) a second set of slots for holding a suture;
    d) a third set of slots forming a tab therebetween for holding the suture;
    e) said guide wire being received in said first set of slots with misalignment of one pair of slots with respect to the other slots causing said guide wire to bow to facilitate frictional retention thereof; and
    f) said suture being coupled to the guide wire, with said suture anchor being situated on said thin body whereby said suture can be grasped at the tab between the third set of slots and pulled to remove said guide wire, suture and suture anchor from said body without causing said suture anchor to travel through a slot.

2. A suture retaining package according to claim 1 wherein the first set of slots comprises at least first, second and third pairs of mutually spaced slots.

3. A suture retaining package according to claim 2 wherein the second set of slots comprises at least two spaced slots laterally misaligned with said first set of slots.

4. A suture retaining package according to claim 3 wherein the third set of slots comprises a pair of spaced slots in said top edge of said card receiving the suture.

5. A suture retaining package according to claim 1, wherein each of said first set of paired slots is substantially aligned laterally in the card.

6. A suture retaining package according to claim 1, wherein each of said second set of slots comprises S-shaped slots.

7. A suture retaining package according to claim 1, wherein said body has a first half and a second half, and a scoring between said halves, whereby said first half may be folded over said second half.

8. A suture retaining package according to claim 7, wherein said first half has a tab aligned with an eighth slot in said second half whereby said tab may be secured in said eighth slot when said first half is folded over said second half to retain said first half in overlying relation to said second half.

9. A suture retaining package according to claim 1, wherein said body is generally rectangular.

10. A suture retaining package according to claim 1, wherein said body is made of plastic.

11. A suture retaining package according to claim 7, wherein said first half has two tabs respectively aligned with closure slots in said second half, whereby when said first half is folded over said second half said tabs may be secured in said closure slots to retain said first half in overlying relation to said second half.

12. A suture retaining package comprising:
    a) a thin body having a front face, a rear face, and a top edge;
    b) a first set of slots comprising at least first, second and third mutually spaced slot pairs, said second slot pair being located between said first and second slot pairs and being laterally misaligned with respect to said first and third slot pairs;
    c) a second set of slots comprising at least fourth and fifth spaced slot pairs laterally misaligned with said first, second and third slots, each of said fourth and fifth slot pairs comprising an S-shaped slot forming a pair of slots; and
    d) a third set of slots comprising a sixth pair of slots in said top edge of said card;
    e) a guide wire being received in said first set of slots with misalignment of said second slot pair with respect to said first and third slot pairs causing said guide wire to bow to facilitate frictional retention thereof;
    f) a suture being received in said second and third sets of slots with a suture anchor being situated on said body whereby said suture may be grasped between said slots of said sixth pair of slots and may be pulled to remove said guide wire, suture and suture anchor from said body without causing said suture anchor to travel through a slot.

13. A suture retaining package according to claim 12, wherein said body is generally rectangular.

14. A suture retaining package according to claim 12, wherein said body is made of plastic.

15. A suture retaining package according to claim 12, wherein said first half has two tabs respectively aligned with two further slots in said second halt whereby when said first half is folded over said second half, said tabs may be secured in said further slots to retain said first half in overlying relation to said second half.

* * * * *